United States Patent [19]

Enloe

[11] Patent Number: 5,415,644

[45] Date of Patent: * May 16, 1995

[54] DIAPERS WITH ELASTICIZED SIDE POCKETS

[75] Inventor: Kenneth M. Enloe, Neenah, Wis.

[73] Assignee: Kimberly-Clark Corporation, Neenah, Wis.

[ * ] Notice: The portion of the term of this patent subsequent to Nov. 3, 2004 has been disclaimed.

[21] Appl. No.: 310,106

[22] Filed: Feb. 13, 1989

Related U.S. Application Data

[63] Continuation of Ser. No. 242,460, Sep. 9, 1988, which is a continuation of Ser. No. 85,422, Aug. 13, 1987, Pat. No. 4,846,823, which is a continuation of Ser. No. 786,891, Oct. 11, 1985, Pat. No. 4,704,116, which is a continuation-in-part of Ser. No. 627,164, Jul. 2, 1984, abandoned.

[51] Int. Cl.⁶ .................. A61F 13/15; A61F 13/20
[52] U.S. Cl. .................. 604/385.2; 604/358; 604/385.1
[58] Field of Search .................. 604/358, 385.1, 385.2, 604/373, 369

[56] References Cited

U.S. PATENT DOCUMENTS

| Re. 26,151 | 1/1967 | Duncan et al. |
| Re. 28,483 | 7/1975 | Ralph . |
| Re. 30,057 | 7/1979 | Schaar . |
| Re. 33,106 | 11/1989 | Beckestrom . |
| 1,419,044 | 6/1922 | Gunderson . |
| 1,508,740 | 9/1924 | Brand . |
| 1,971,671 | 8/1934 | Alsop . |
| 1,977,604 | 10/1934 | Alsop . |
| 2,004,088 | 6/1935 | Alsop . |
| 2,026,158 | 12/1935 | Bennett . |
| 2,052,598 | 9/1936 | Berg . |
| 2,078,512 | 4/1937 | Simpson . |
| 2,141,105 | 12/1938 | Eller et al. . |
| 2,201,255 | 5/1940 | Wilson . |
| 2,419,867 | 4/1947 | Woodman . |
| 2,468,445 | 4/1949 | Hurst . |
| 2,509,674 | 5/1950 | Cohen . |
| 2,538,758 | 1/1951 | Bricmont . |
| 2,544,069 | 3/1951 | Cutler . |
| 2,545,674 | 3/1951 | Ralph . |
| 2,575,164 | 11/1951 | Donovan . |
| 2,616,427 | 11/1952 | Pettit . |
| 2,662,526 | 12/1953 | Sanford . |
| 2,675,805 | 4/1954 | Trimble . |
| 2,787,271 | 4/1957 | Clark . |
| 2,827,052 | 3/1958 | Goodman . |
| 2,840,077 | 6/1958 | Morgan . |
| 2,893,393 | 7/1959 | Pressley . |
| 2,895,477 | 7/1959 | Bernard . |
| 2,916,037 | 12/1959 | Hansen . |

(List continued on next page.)

FOREIGN PATENT DOCUMENTS

| 86044/82 | 7/1982 | Australia . |
| 21332/83 | 11/1983 | Australia . |
| 2133283 | 5/1984 | Australia . |
| 4521785 | 2/1986 | Australia . |

(List continued on next page.)

*Primary Examiner*—Randall L. Green
*Assistant Examiner*—P. Zuttarelli
*Attorney, Agent, or Firm*—Willian Brinks Hofer Gilson & Lione

[57] ABSTRACT

A garment with a backsheet (12), a bodyside liner (14) essentially coterminous with the backsheet (12) and forming a shape with a front waist section (18), a back waist section (20) and side sections connecting the front waist section (18) to the back waist section (20) and first and second flaps (30, 32) formed from or attached to bodyside liner (14). Flaps (30, 32) may have elastic members (40, 42) applied thereto respectively. Flaps (30, 32) may be folded inwardly and respective ends thereof may be bonded to bodyside liner (14) so that edges of flaps are directed toward a centerline (38) of the garment. The flaps (30, 32) may be attached to or formed from bodyside liner (14) along lines (34, 36) which are parallel to centerline (38) or which diverge from or converge toward centerline (38). Additionally, flaps (30, 38) may have varying width and be less than full length.

26 Claims, 6 Drawing Sheets

5,415,644
Page 2

U.S. PATENT DOCUMENTS

| | | | |
|---|---|---|---|
| 2,964,040 | 12/1960 | Ashton et al. | |
| 2,969,065 | 1/1961 | Farnsworth | 604/386 |
| 3,000,381 | 9/1961 | Mulhole et al. | |
| 3,180,335 | 4/1965 | Duncan et al. | |
| 3,182,661 | 5/1965 | Ribeiro et al. | |
| 3,339,548 | 9/1967 | Seltzer | |
| 3,349,769 | 10/1967 | Piekarski | |
| 3,364,931 | 1/1968 | Hirsh | |
| 3,386,442 | 6/1968 | Sabee | |
| 3,417,751 | 12/1968 | Murdoch | |
| 3,426,755 | 2/1969 | Romanek | |
| 3,452,753 | 7/1969 | Sanford | |
| 3,461,872 | 8/1969 | McConnell et al. | |
| 3,481,337 | 12/1969 | Ruffo | |
| 3,509,881 | 5/1970 | Sabee | |
| 3,530,859 | 9/1970 | Heimowitz | |
| 3,532,093 | 10/1970 | Lovret | |
| 3,572,342 | 3/1971 | Lindquist et al. | |
| 3,575,174 | 4/1971 | Mogor | |
| 3,592,194 | 7/1971 | Duncan | |
| 3,593,716 | 7/1971 | Vogt | |
| 3,612,055 | 10/1971 | Mesek | |
| 3,658,063 | 4/1972 | Schaar | |
| 3,658,064 | 4/1972 | Pociluyko | |
| 3,665,920 | 5/1972 | Davis | |
| 3,667,466 | 6/1972 | Ralph | |
| 3,710,797 | 1/1973 | Marsan | |
| 3,744,494 | 7/1973 | Marsen | |
| 3,771,524 | 11/1973 | Ralph | |
| 3,776,233 | 12/1973 | Schaar | |
| 3,779,246 | 12/1973 | Mesek et al. | |
| 3,807,402 | 4/1974 | Miller et al. | |
| 3,825,006 | 7/1974 | Ralph | |
| 3,848,594 | 11/1974 | Buell | |
| 3,860,003 | 1/1975 | Buell | |
| 3,881,488 | 5/1975 | Delanty et al. | |
| 3,884,234 | 5/1975 | Taylor | |
| 3,885,568 | 5/1975 | Schaar | |
| 3,890,973 | 6/1975 | Davis et al. | |
| 3,913,578 | 10/1975 | Schaar | |
| 3,920,017 | 11/1975 | Karami | |
| 3,929,134 | 12/1975 | Karami | |
| 3,930,501 | 1/1976 | Schaar | |
| 3,930,502 | 1/1976 | Tritsch | |
| 3,938,522 | 2/1976 | Repke | |
| 3,943,930 | 3/1976 | Schaar | |
| 3,952,745 | 4/1976 | Duncan | |
| 3,965,906 | 6/1976 | Karami | |
| 3,978,861 | 9/1976 | Schaar | |
| 3,987,794 | 10/1976 | Schaar | |
| 3,995,637 | 12/1976 | Schaar | |
| 3,995,640 | 12/1976 | Schaar | |
| 3,999,547 | 12/1976 | Hernandez | |
| 3,999,548 | 12/1976 | Hernandez | |
| 4,029,100 | 6/1977 | Karami | |
| 4,040,423 | 8/1977 | Jones, Sr. | |
| 4,041,949 | 8/1977 | Kozak | |
| 4,041,950 | 8/1977 | Jones, Sr. | |
| 4,044,769 | 8/1977 | Papajohn | |
| 4,050,462 | 9/1977 | Woon et al. | |
| 4,069,822 | 1/1978 | Buell | |
| 4,077,410 | 3/1978 | Butterworth et al. | 604/372 |
| 4,081,301 | 3/1978 | Buell | |
| 4,090,515 | 10/1985 | Karami | |
| 4,100,324 | 7/1978 | Anderson et al. | |
| 4,100,922 | 7/1978 | Hernandez | |
| 4,129,132 | 12/1978 | Butterworth et al. | |
| 4,166,464 | 9/1979 | Korpman | |
| 4,182,336 | 1/1980 | Black | |
| 4,187,342 | 2/1980 | Holst et al. | |
| 4,200,102 | 4/1980 | Duhamel et al. | |
| 4,210,143 | 7/1980 | De Jonckheere | |
| 4,210,144 | 7/1980 | Sarge, III | |
| 4,226,238 | 10/1980 | Bianco | |
| 4,227,952 | 10/1980 | Sabee | |
| 4,232,674 | 11/1980 | Melican | |
| 4,239,578 | 12/1980 | Gore | |
| 4,246,900 | 1/1981 | Schroeder | |
| 4,253,461 | 3/1981 | Strickland et al. | |
| 4,261,782 | 4/1981 | Teed | |
| 4,285,383 | 8/1981 | McNair | |
| 4,309,236 | 1/1982 | Teed | |
| 4,315,508 | 2/1982 | Bolick | |
| 4,319,572 | 3/1982 | Widlund et al. | |
| 4,323,070 | 4/1982 | Ternstrom et al. | |
| 4,324,245 | 4/1982 | Mesek et al. | |
| 4,325,372 | 4/1982 | Teed | |
| 4,326,528 | 4/1982 | Ryan et al. | |
| 4,333,466 | 6/1982 | Matthews | |
| 4,388,075 | 6/1983 | Meske et al. | |
| 4,397,645 | 8/1983 | Buell | |
| 4,413,996 | 11/1983 | Taylor | |
| 4,425,127 | 1/1984 | Suzuki et al. | |
| 4,425,128 | 1/1984 | Motomura | |
| 4,425,178 | 1/1984 | Frick | |
| 4,430,086 | 2/1984 | Repke | |
| 4,486,192 | 12/1984 | Sigl | |
| 4,488,927 | 12/1984 | Hooper | |
| 4,490,148 | 12/1984 | Beckestrom | |
| 4,496,359 | 1/1985 | Pigneul | |
| 4,496,360 | 1/1985 | Joffe et al. | |
| 4,498,944 | 2/1985 | Krause et al. | |
| 4,500,316 | 2/1985 | Damico | 604/389 |
| 4,527,989 | 7/1985 | Karami | |
| 4,560,380 | 12/1985 | Tharel | 604/385 R |
| 4,578,071 | 3/1986 | Buell et al. | |
| 4,578,073 | 3/1986 | Dysart et al. | 604/397 |
| 4,579,556 | 4/1986 | McFarland | 604/385 A |
| 4,589,876 | 5/1986 | Van Tilburg | |
| 4,597,760 | 7/1986 | Buell | |
| 4,597,761 | 7/1986 | Buell | 604/397 |
| 4,601,717 | 7/1986 | Blevins | |
| 4,623,342 | 11/1986 | Ito et al. | |
| 4,626,305 | 12/1986 | Suzuki et al. | |
| 4,636,207 | 1/1987 | Buell | |
| 4,657,539 | 4/1987 | Hasse | 604/385 R |
| 4,662,877 | 5/1987 | Williams | 604/385 A |
| 4,687,477 | 8/1987 | Suzuki et al. | |
| 4,687,478 | 8/1987 | Van Tilburg | |
| 4,692,163 | 9/1987 | Widlund et al. | |
| 4,695,278 | 9/1987 | Lawson | |
| 4,701,177 | 10/1987 | Ellis et al. | |
| 4,704,115 | 11/1987 | Buell | 604/385 A |
| 4,704,116 | 11/1987 | Enloe | 604/385 A |
| 4,710,187 | 12/1987 | Boland et al. | |
| 4,738,676 | 4/1988 | Osborn | 604/385 R |
| 4,738,677 | 4/1988 | Foreman | |
| 4,743,246 | 5/1988 | Lawson | |
| 4,753,646 | 6/1988 | Enloe | |
| 4,775,375 | 10/1988 | Aledo | |
| 4,795,454 | 1/1989 | Dragoo | |
| 4,808,177 | 2/1989 | DesMarais et al. | |
| 4,808,178 | 2/1989 | Aziz et al. | 604/385.2 |
| 4,816,025 | 3/1989 | Foreman | |
| 4,822,435 | 4/1989 | Igaue et al. | |
| 4,938,754 | 7/1990 | Mesek | |
| 5,085,654 | 2/1992 | Buell | |
| 5,246,431 | 9/1993 | Minetola et al. | 604/385.1 |
| 5,254,111 | 10/1993 | Cancio et al. | 604/385.1 |
| 4,846,823 | 7/1989 | Enloe | 604/385.2 |
| 4,863,482 | 9/1989 | Junino et al. | |
| 4,883,482 | 11/1989 | Gandrez et al. | |
| 4,892,528 | 1/1990 | Suzuki et al. | |
| 4,900,317 | 2/1990 | Buell | |
| 4,909,803 | 3/1990 | Aziz et al. | |

FOREIGN PATENT DOCUMENTS

| | | |
|---|---|---|
| 188667 | 2/1957 | Austria . |
| 1175602 | 10/1984 | Canada . |
| 1211902 | 9/1986 | Canada . |
| 1216702 | 1/1987 | Canada . |
| 1238151 | 6/1988 | Canada . |
| 1302654 | 6/1992 | Canada . |
| 0070584 | 1/1983 | European Pat. Off. . |
| 0091412 | 10/1983 | European Pat. Off. . |
| 0109126 | 5/1984 | European Pat. Off. . |
| 0149999 | 7/1985 | European Pat. Off. . |
| 183668 | 6/1986 | European Pat. Off. . |
| 190881 | 8/1986 | European Pat. Off. . |
| 0130848 | 11/1987 | European Pat. Off. . |
| 251332 | 1/1988 | European Pat. Off. . |
| 268858 | 6/1988 | European Pat. Off. . |
| 0134086 | 1/1989 | European Pat. Off. . |
| 304631 | 3/1989 | European Pat. Off. . |
| 2425205 | 5/1978 | France . |
| 2573629 | 11/1984 | France . |
| 2557774 | 7/1985 | France . |
| 2561078 | 7/1985 | France . |
| 1070779 | 12/1959 | Germany . |
| 1435861 | 2/1969 | Germany . |
| 2455778 | 6/1975 | Germany . |
| 2657220 | 7/1977 | Germany . |
| 2657221 | 7/1977 | Germany . |
| 3128828 | 4/1982 | Germany . |
| 3141963 | 5/1982 | Germany . |
| 3319043 | 5/1983 | Germany . |
| 39-33810 U | 11/1964 | Japan . |
| 39-33813 U | 11/1964 | Japan . |
| 40-1543 U | 1/1965 | Japan . |
| 40-11543 U | 4/1965 | Japan . |
| 40-21930 U | 7/1965 | Japan . |
| 41-17377 U | 8/1966 | Japan . |
| 41-18031 U | 8/1966 | Japan . |
| 41-18359 U | 8/1966 | Japan . |
| 4118359 | 8/1966 | Japan . |
| 42-7943 U | 4/1967 | Japan . |
| 42-9064 U | 5/1967 | Japan . |
| 42-11718 U | 6/1967 | Japan . |
| 220865 | 5/1968 | Japan . |
| 51-18024 U | 5/1976 | Japan . |
| 52-132221 U | 10/1977 | Japan . |
| 55-10169 U | 1/1980 | Japan . |

DIAPERS WITH ELASTICIZED SIDE POCKETS

CROSS REFERENCE TO RELATED APPLICATIONS

This is a continuation of application Ser. No. 242,460, filed Sep. 9, 1988; which is a continuation of application Ser. No. 85,422, filed Aug. 13, 1987, now U.S. Pat. No. 4,846,823, issued Jul. 11, 1989; which is a continuation of application Ser. No. 786,891, filed Oct. 11, 1985, now U.S. Pat. No. 4,704,116, issued Nov. 3, 1987, and for which a Certificate of Correction issued Apr. 12, 1988; which is a continuation-in-part of application Ser. No. 627,164, filed Jul. 2, 1984, and now abandoned.

TECHNICAL FIELD

The present invention relates, generally, to the field of disposable garments utilized for the absorption and containment of urine and other body exudates. More particularly, the present invention relates to disposable garments with a provision for the containment of urine and liquid fecal material. Most particularly, the present invention relates to disposable garments that provide enhanced containment of urine and liquid fecal material with elasticized side pockets or flaps formed from or attached to a bodyside liner of the disposable garment.

BACKGROUND ART

Disposable garments are generally well known in the art and have become an important and essentially indispensable sanitary protection item, most particularly in the field of infant and child care where disposable diapers provide for the absorption and containment of urine and other body exudates. Present commercially available disposable diapers are generally unitary, pre-shaped and prefolded, and comprised of a liquid pervious bodyside liner, a fluid impervious backing sheet with an absorbent material disposed therebetween. These presently available disposable diapers have met a particular need and have become ever increasingly popular. However, even though the presently available disposable diapers are efficient and effective, they have several drawbacks that have been identified by mothers of infants wearing the diapers. Although the presently available diapers have elasticized leg openings which provide a better fit and enhanced containment of fluid exudates, they have not been entirely successful in stopping leakage from explosive liquified bowel movements and rapid discharges of urine.

Another drawback associated with presently commercially available disposable diapers is skin irritation caused by urine, feces or moisture trapped next to the skin. The feces, if remaining next to the skin, can smear causing problems in cleanup.

The attempts to solve these drawbacks associated with the present commercially available disposable diapers have extended over several years and include several different concepts. For example, U.S. Pat. No. 3,999,547 to Hernandez discloses a disposable diaper with a waterproof back sheet, a hydrophobic sheet, and an absorbent pad sandwiched between the back sheet and the face sheet. The diaper is folded to define a box pleated configuration having a central panel, inwardly extending panels and outwardly extending panels with the inner edges of the inwardly extending panels being in abutting relationship. Sealing strips of waterproof material separate from the back sheet are secured on the face sheet. The sealing strips are formed by folding an excess width of the back sheet over the face sheet forming side flap portions, and then cutting the side flap portions free from the back sheet. The sealing strips may be folded inwardly toward the center of the diaper to form fluid catching seals.

A similar concept is disclosed in U.S. Pat. No. 4,210,143 to De Jonckheere which discloses a disposable diaper for a baby with at least one sheet of flexible liquid impermeable material comprising two longitudinal edges intended to define a waist portion and an absorbent pad superimposed on a central region of the liquid impermeable sheet. The diaper is characterized, in that it comprises, respectively in the immediate vicinity of each of the longitudinal edges, on either side of the pad, a flexible longitudinal sheath inside which a flexible longitudinal tie is able to slide and in that each sheath comprises means for gaining access to the corresponding flexible tie in order to enable the latter to be gripped manually and to be tensioned at will in order to reduce the apparent length of the longitudinal edges, to press the latter at will around the baby's legs and to give the disposable diaper the shape of a trough between the legs.

Another concept is shown in U.S. Pat. No. 4,490,148 to Beckestrom which discloses a protector against incontinence comprising an oblong absorbent body which is fixed to a bottom liquid-tight layer extending outside the absorbent body. The lateral edge portions of the layer are folded in over the absorbent body and form side flaps, the distance between the edges thereof being less than the width of the absorbent body at its mid section. The side flaps are fixed at their ends to the bottom layer. An elastic line, arranged at the edge of each side flap, is designed to contract itself and thereby the edges of the side flaps. When the protector is put on, the edges of the side flaps come into elastic sealing contact in the thigh crease of the crotch.

However, these attempts to solve one problem have resulted in the emergence of other problems. For example, the elasticized flaps can cause the waterproof material of the flaps to provide a tight seal at the thigh crease because the tensioned elastic presses the easily deformable flaps into close contact with the skin. The waterproof material of the flaps can then cause urine or moisture and even liquid fece material to collect next to the skin and cause skin irritation.

The present application teaches an improved disposable garment which provides fluid pervious flaps to enhance the containment and absorption of urine and other fluid exudates as well as solid exudates. The flaps, made up of water pervious material, slows the sideways flow of fluidic material and stops essentially all the sideways flow of solid material. Furthermore, the flaps enhance skin dryness by causing at least one extra layer of material to be disposed between the absorbent area of the diaper and the skin of the wearer. This, in addition to having fecal material separated from the skin by at least one layer of flap material, decreases the potential of skin irritation.

DISCLOSURE OF THE INVENTION

It has now been determined in accordance with the present invention that the disposable diaper with side pockets or flaps can be produced that enhances the containment and absorption of urine and other fluid body exudates, such as liquified fecal material. Advantageously, the disposable diaper of the present invention achieves decreased leakage of urine and other fluid body exudates from around the leg areas of the disposable diaper.

The foregoing, and other advantages of the present invention, are realized in a disposable garment with a back sheet, a bodyside liner essentially coterminous with the back sheet forming a shape with a front waist section and a back waist section with two side sections connecting the front waist section to the back waist section and a pair of flaps, attached to or formed from, the bodyside liner. Each respective flap is disposed inwardly of the respective side sections. The flaps may be essentially rectangular in shape with first and second longitudinal sides essentially parallel to a centerline of the garment wherein the centerline lies between the respective side sections. The longitudinal sides are connected by base sides and both the longitudinal sides and the base sides have preselected dimensions. The longitudinal sides may have a length sufficient to extend from the front waist section to the back waist section. The base sides may have a width in the range from about one-half inch to a width sufficient for a longitudinal side of each flap to be essentially coterminous with the centerline of the garment.

Each flap may have at least one elastic member disposed therein. The elastic member may be applied to the flap with a tension sufficient to cause the flap to conform to the wearer's shape. The elastic member may be applied to the distal longitudinal edge of the flap. Each flap may also have a second elastic member applied. The second elastic member may be applied intermediate the first elastic member and the other longitudinal side of the flap. The second elastic member may be applied with a tension greater than, less than or equal to the tension of the first elastic member wherein the two elastic members cooperate to cause the flaps to conform to the shape of the wearer.

The flaps may be attached to or formed from the bodyside liner along a pair of curved lines disposed symmetrically on each side of a centerline of the garment. The curved lines may diverge from the centerline in a direction away from the center portion of the garment or the curved lines may converge toward the centerline.

In either case the flaps may have a length sufficient to cover only a portion of the length of the garment. In addition, the width of the flaps may vary. The width may be wider at the ends of the flaps and narrower at the center of the flaps or the width of the flaps may be narrower at the ends of the flaps and wider at the center of the flaps.

Other aspects of the present invention in terms of both construction and mode of operation, as well as fuller appreciation for its manufacture and use, will be gained from an examination of the following detailed description of the modes for carrying out the invention, read in conjunction with the figures of the drawing.

MODES FOR CARRYING OUT THE INVENTION

The present invention relates, generally, to disposable garments utilized for the absorption and containment of urine and other body exudates. The present invention relates more specially to disposable garments that are utilized for the absorption and containment of liquids and fluidic body exudates such as fluidic fecal material. Most particularly, the present invention provides at least one pair of waste containment flaps or barrier cuffs, which may be elasticized, to slow the sideways flow of liquids, such as urine, and to essentially prevent the sideways flow of fluidic solids, such as fluidic fecal material. Accordingly, the present invention will now be described with reference to certain modes for carrying out the invention within the aforementioned context. Those skilled in the art will realize that such a description is meant to be exemplary only and should not be deemed limitative respecting the scope of the present invention, for example, in terms of its construction.

Figure 1:
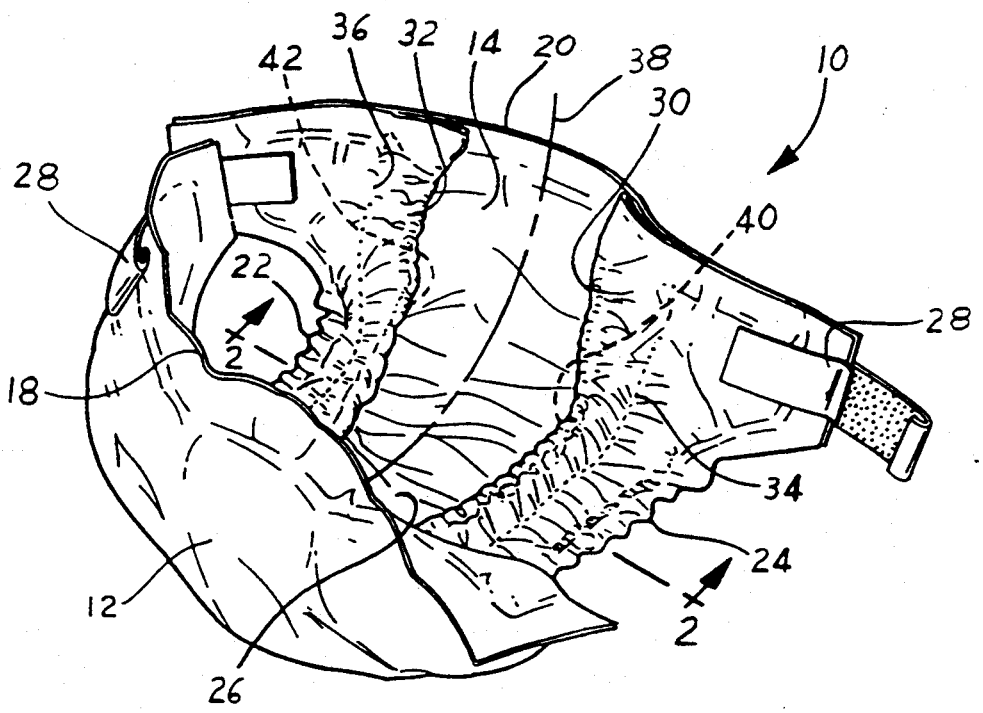
FIG. 1 is a perspective view of the garment of the present invention.
Figure 2:
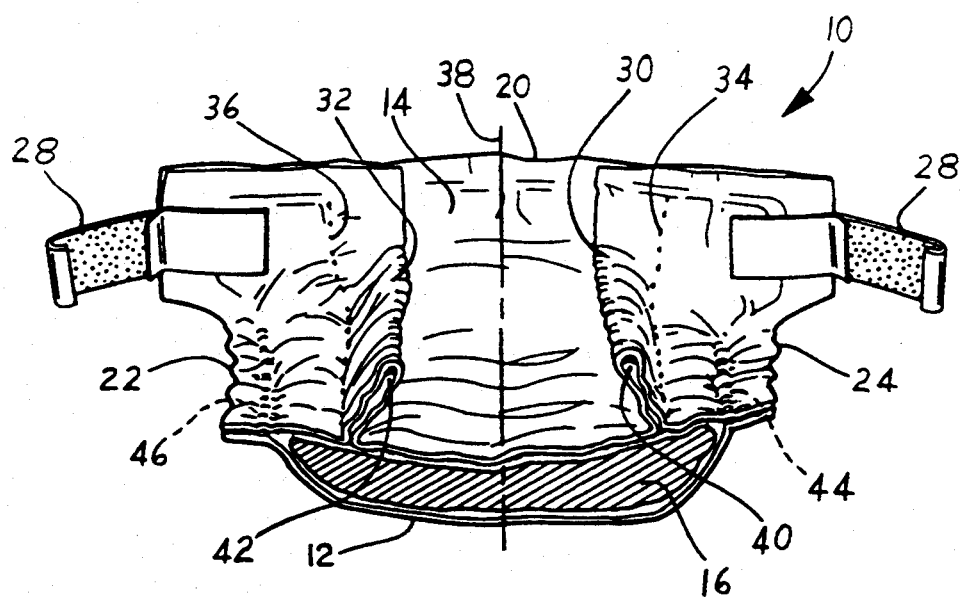
FIG. 2 is a half-perspective view showing a sectional view of cross section 2—2 as shown in FIG. 1.

Turning to the figures, in each of which like parts are identified with like reference characters, FIG. 1 is a perspective view of an integral disposable garment, or absorbent article in this case, a disposable diaper 10. FIG. 2 is a perspective view of the disposable diaper 10 showing sectional view of cross section 2—2 as shown in FIG. 1. The disposable diaper 10 typically comprises a backsheet 12, a bodyside liner or liquid-pervious topsheet 14, to which the backsheet 12 is connected, and an absorbent cone, body or pad 16 disposed between backsheet 12 and bodyside liner 14. As used herein, "associated" and "connected" encompass configurations in which the topsheet is directly joined to the backsheet by affixing the topsheet directly to the backsheet, and configurations in which the topsheet is indirectly joined to the backsheet by affixing the topsheet to intermediate members which in turn are affixed to the backsheet. The bodyside liner 14 is made from a liquid pervious material and backsheet 12 is made from a liquid impervious material. The bodyside liner 14 and backsheet 12 are essentially coterminous and form a shape with a back waist section or region 20, a front waist section or region 18 and two side sections, or elastically contractible gasketing cuffs, indicated by numerals 22, 24. Intermediate the front waist section 18 and back waist section 20 is a crotch section, or region indicated by numeral 26. The gasketing cuffs 22, 24 are disposed adjacent each longitudinal edge of the absorbent article in at least the crotch section, and comprise a flexible side flap extending from and along the side edge of the absorbent body 16 in at least the crotch section of the absorbent article. The longitudinal edges of the absorbent article are the edges which extend from the front waist region along the crotch region to the back waist region. The garment is typically placed around a wearer, such as an infant, and held in place with fastening means, such as tapes shown at 28. Other fastening means can be used without departing from the scope of the present invention. A pair of barrier cuffs or flaps 30, 32 are attached to or formed from bodyside liner 14 along lines 34, 36 respectively, and are thus integral or unitary with bodyside liner 14 and side sections 22, 24. The term "integral" as used herein with respect to the barrier cuffs or flaps being integral with the bodyside liner means that the barrier cuffs or flaps are separate elements whose proximal edge is directly or indirectly attached to the topsheet. The term "integral disposable absorbent article" as used herein is a single-unit disposable absorbent article which is adapted for use within the addition of any further absorbent component by the user. The term "unitary" as used herein means that the barrier cuffs or flaps are made or formed from the same element or material as the topsheet, so that the proximal edge is a continuous and undivided element of the topsheet. The proximal edges of the barrier cuffs or flaps 30, 32 are disposed adjacent the gasketing cuffs or side sections 22, 24, and the distal edges of the barrier cuffs or flaps 30, 32 are disposed inboard of the proximal edges. In either case the crease formed along lines 34, 36 may be "sealed" i.e., by a continuous sonic bond or by a strip of adhesive. The sealing of the crease increases the stability of the structure to maintain its shape and increases the resistance to leakage. Alternatively, the crease can consist of a series of spotbonds. The flaps 30, 32 are attached to, or formed from bodyside liner 14, and are disposed adjacent to, and inboard or inwardly of, sides 24, 22 respectively. As can be appreciated, if flaps 30, 32 are formed from bodyside liner 14, the flaps are the same material as bodyside liner 14. However, if the flaps are attached to bodyside liner 14, the flaps 30, 32 may be made from a different material. The preferred material for flaps 30, 32 is a liquid pervious material. The flaps 30,32 may be folded inwardly toward a centerline 38 and bonded at each end to the bodyside liner 14. Flaps 30, 32 form pockets into which solid fecal material collects and is contained. Alternately, fluidic fecal material is collected by the pockets and is essentially strained allowing the liquid portion to be absorbed by the absorbent pad or body of the garment. Flaps 30, 32 may have at least one spacing and tensioning elastic member, indicated at 40, 42, applied and secured thereto, which serves as a tensioning and spacing means attached to the flaps 30, 32 for tensioning the barrier cuffs and for spacing a portion of the distal edges of the flaps 30, 32 away from the top surface of the bodyside liner 14, whereby a channel is formed between each barrier cuff and the topsheet; and as a means for shortening or contracting the length of the flaps 30, 32 in comparison to the length of the longitudinal edge of the absorbent article. The elastically contractible gasketing cuffs 22, 24 and the barrier cuffs or flaps 30, 32 thus present an effective means against soiling of a wearer's garments. As indicated in FIGS. 1 and 2, the spacing and tensioning elastic members 40, 42 may be applied essentially at the inwardly directed edge of flaps 30, 32. Also indicated in FIGS. 1 and 2, the disposable garment may additionally have flap elastic members indicated at 44, 46 in the side portions of the garment, which correspond to the leg sections of the garment, the flap elastic members being secured to the side flaps in an elastically contractible condition, whereby the elastically contractible side sections 22, 24 form effective barriers about a wearer's legs. The proximal edges of the flaps 30, 32 are disposed in the side flaps between the flap elastic members and the side edges of the absorbent body or pad 16 in at least the crotch section, the distal edges of the flaps 30, 32 being free from attachment in at least the crotch section. A preferred method of imparting elasticity to the leg sections and the flaps is by extruding a hot melt pressure-sensitive elastomeric adhesive, such as that marketed by H. B. Fuller Company of St. Paul, Minn., U.S.A. under the trademark FULLASTIC. In addition, the elastic members may also comprise any of the usual elastics (e.g., elastic strands) utilized in the diaper making art such as the utilization of a thin ribbon of natural rubber, etc.

Figure 3:
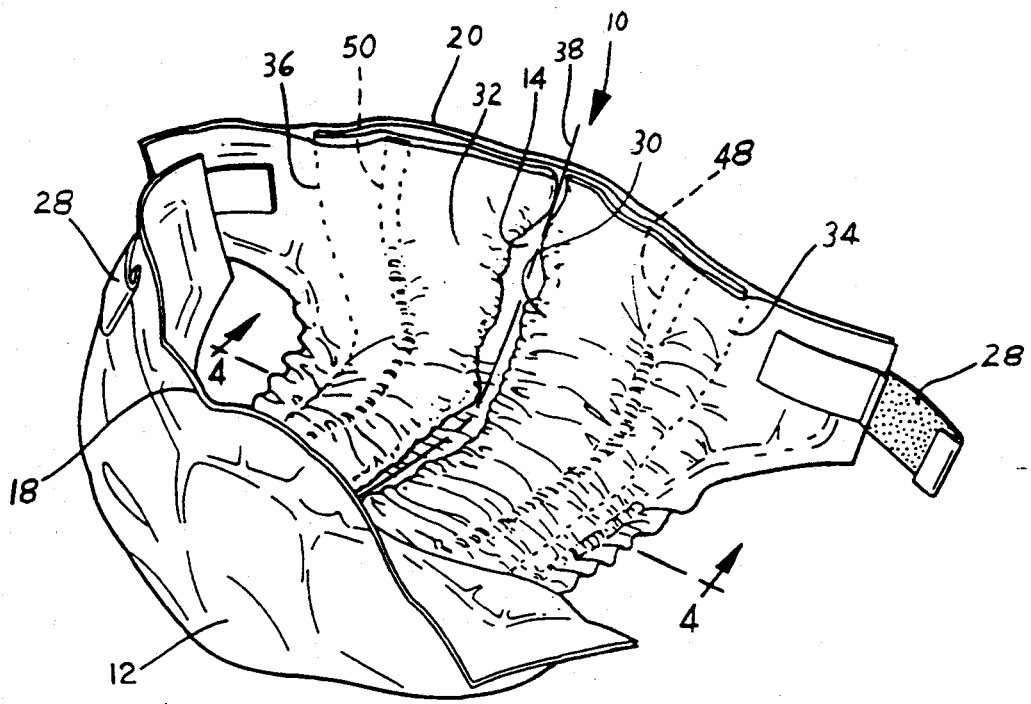
FIG. 3 is a perspective view of an alternative embodiment of the garment of the present invention.
Figure 4:
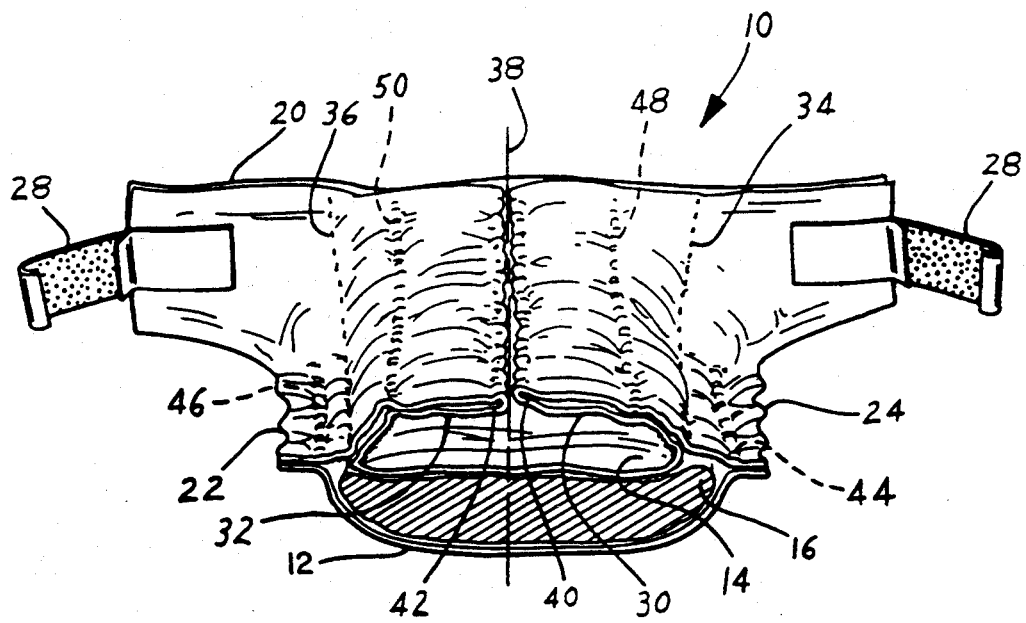
FIG. 4 is a half-perspective view showing a sectional view of cross section 4—4 as shown in FIG. 3.

Referring now to FIGS. 3 and 4, there is shown a perspective view of an alternative embodiment of a garment of the present invention. In this alternative embodiment, flaps 30, 32 have a width sufficient so that inwardly directed edges of the flaps are essentially coterminous with centerline 38. In addition, flaps 30, 32 may have at least a second elastic member 48, 50 disposed in respective flaps. The second elastic member is applied to the flap intermediate to the first elastic member and the lines 34, 36 respectively. The first elastic member in each flap is applied with a first preselected tension sufficient to cause each flap to conform to the shape of a wearer. The second elastic member in each flap, if applied, is applied with a second preselected tension which may be greater than, less than or equal to the first preselected tension. However, the tensions are selected to cooperate so that the flaps conform to the shape of a wearer. The width of the flaps can be from about one-half inch to a width sufficient for the inwardly directed edge of each flap to be essentially coterminous with the centerline 38 as shown in FIGS. 3 and 4.

Figure 5:
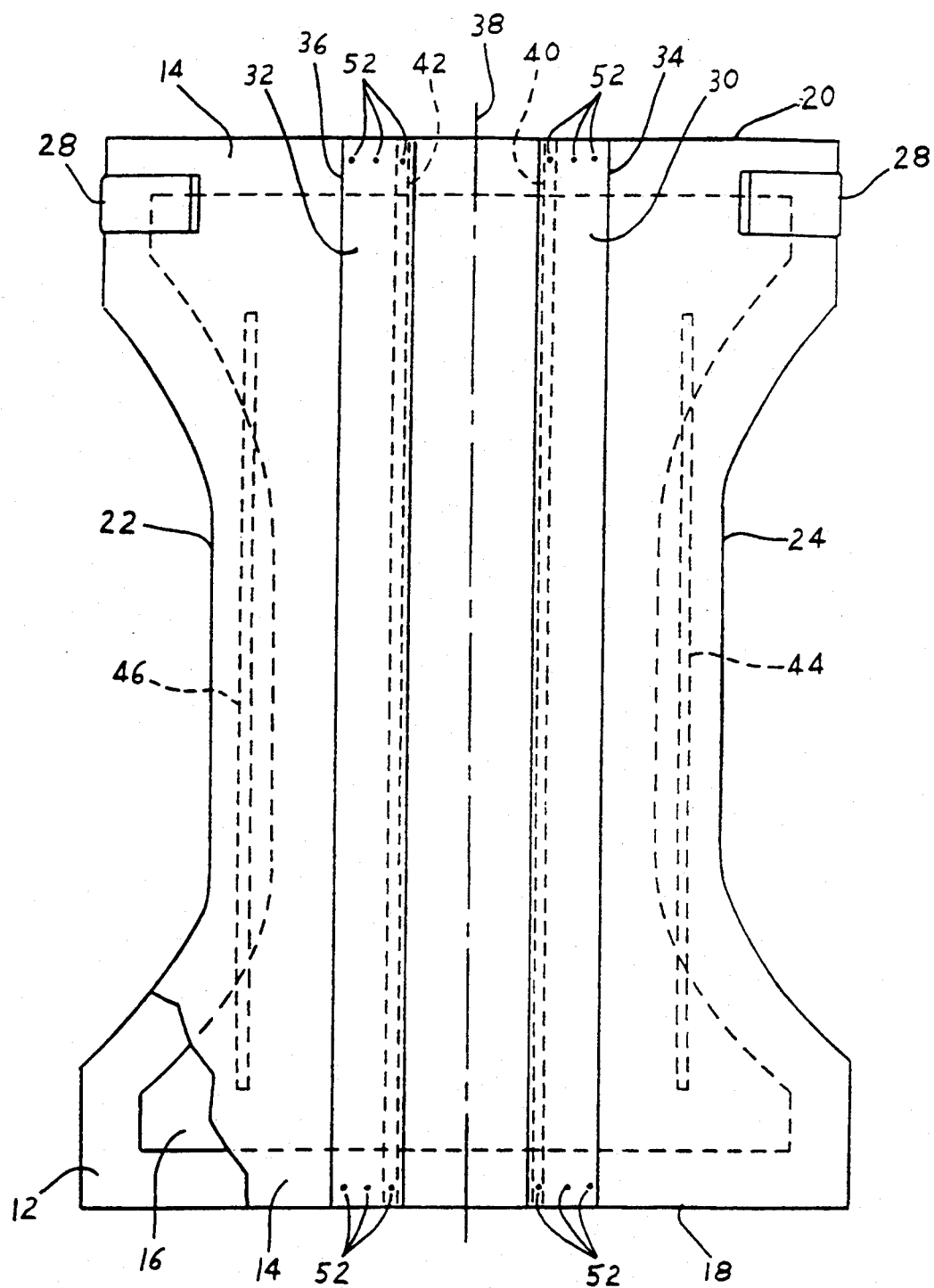
FIG. 5 is a plan view of a garment of the present invention showing full length flaps with an elastic member in each flap.

FIG. 5 is a plan view of a preferred embodiment of the present invention showing flaps 30, 32 with elastic members 40, 42 applied to flaps 30, 32 respectively. Adhesive means or bonds 52 disposed adjacent each of the ends of the flaps 30, 32 bond respective ends of flaps 30, 32 to bodyside liner 14 at the front waist section 18 and back waist section 20, securing closed a portion of flaps 30, 32, a portion of the distal edge in at least the crotch section remaining free from attachment so as to be spaced away from the top surface of bodyside liner 14. Any method of bonding may be used. A preferable method of bonding is autogenous bonding such as sonic bonding. Another method that is acceptable is adhesive bonding.

Figure 6:
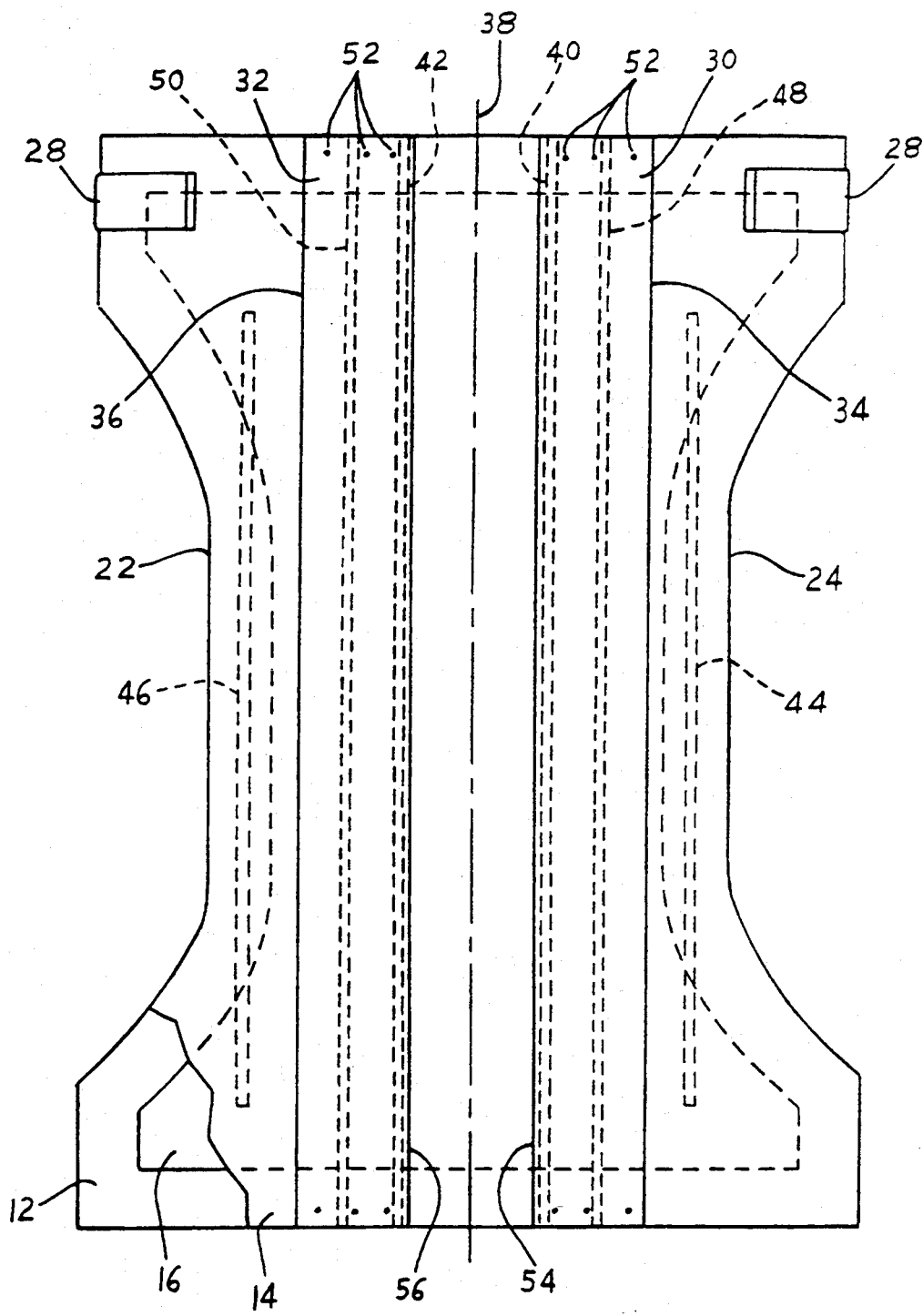
FIG. 6 is a plan view of a garment of the present invention showing full length flaps with two elastic members in each flap.

FIG. 6 is a plan view of an alternative embodiment of the present invention showing flaps 30, 32 having more width and having at least second elastic members 48, 50 applied to flaps 30, 32 respectively. The second elastic members are applied intermediate to lines 34, 36 and inwardly directed edges 54, 56 of flaps 30, 32. Again it should be noted that the width of flaps 30, 32 can vary and the illustrations and descriptions herein are for illustrative purposes only.

Figure 7:
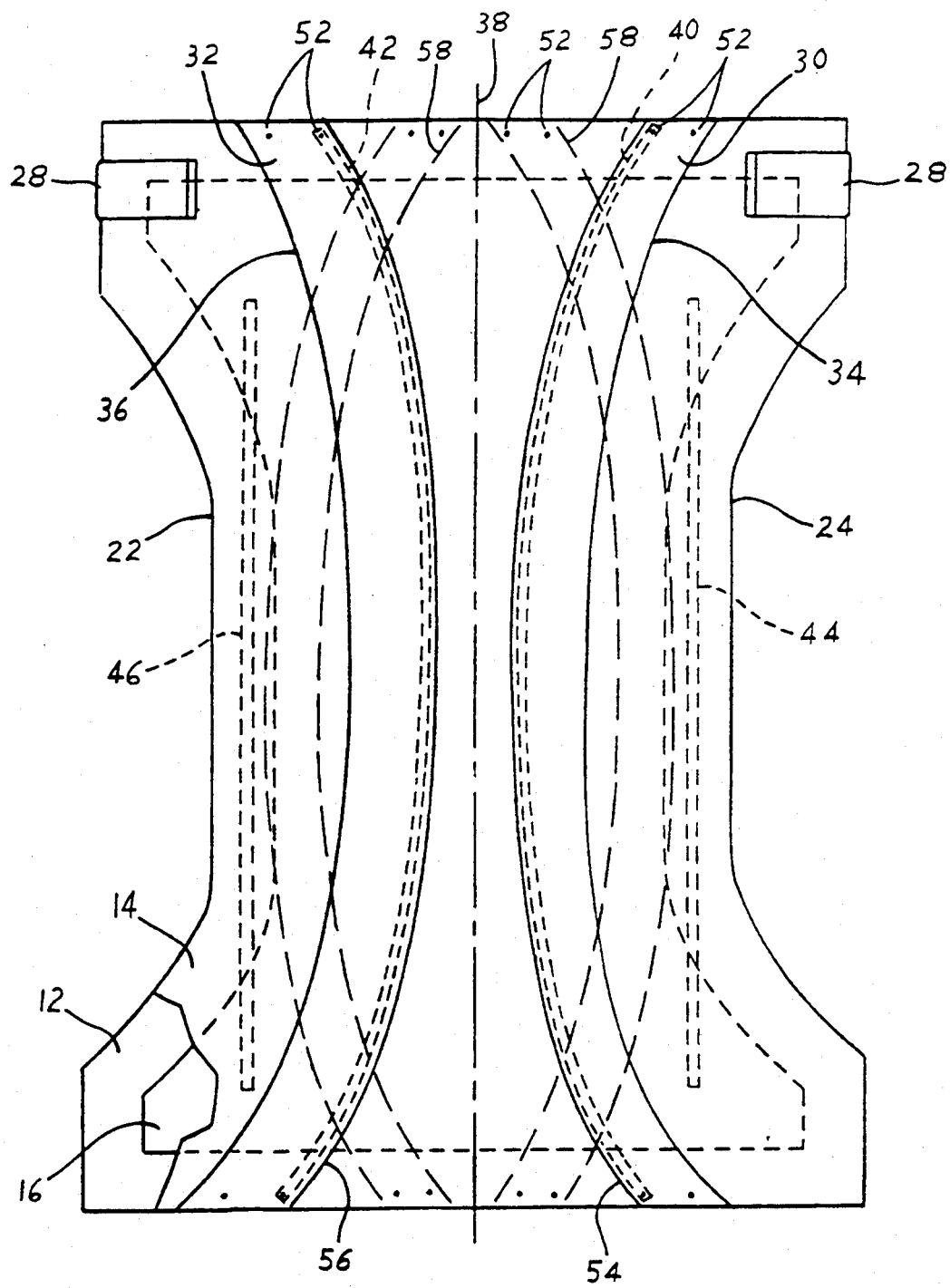
FIG. 7 is a plan view of a garment of the present invention showing full length curved flaps.

FIG. 7 is a plan view of further alternative embodiments of the garment of the present invention, wherein the flaps 30, 32 and flap elastic members 40, 42 are curvilinear. Illustrated therein are flaps 30, 32 which are formed from or attached to inner liner 14 along lines 34, 36 respectively and lines 34, 36 are curved in relation to centerline 38. The lines 34, 36 may diverge from centerline 38 or the lines 34, 36 may converge toward the centerline 38 as shown by phantom line 58. As before flaps 30, 32 may be folded and bonded to inner liner 14 at respective ends of each flap. The flaps are folded and bonded whereby edges 54, 56 are directed toward centerline 38.

Figure 8:
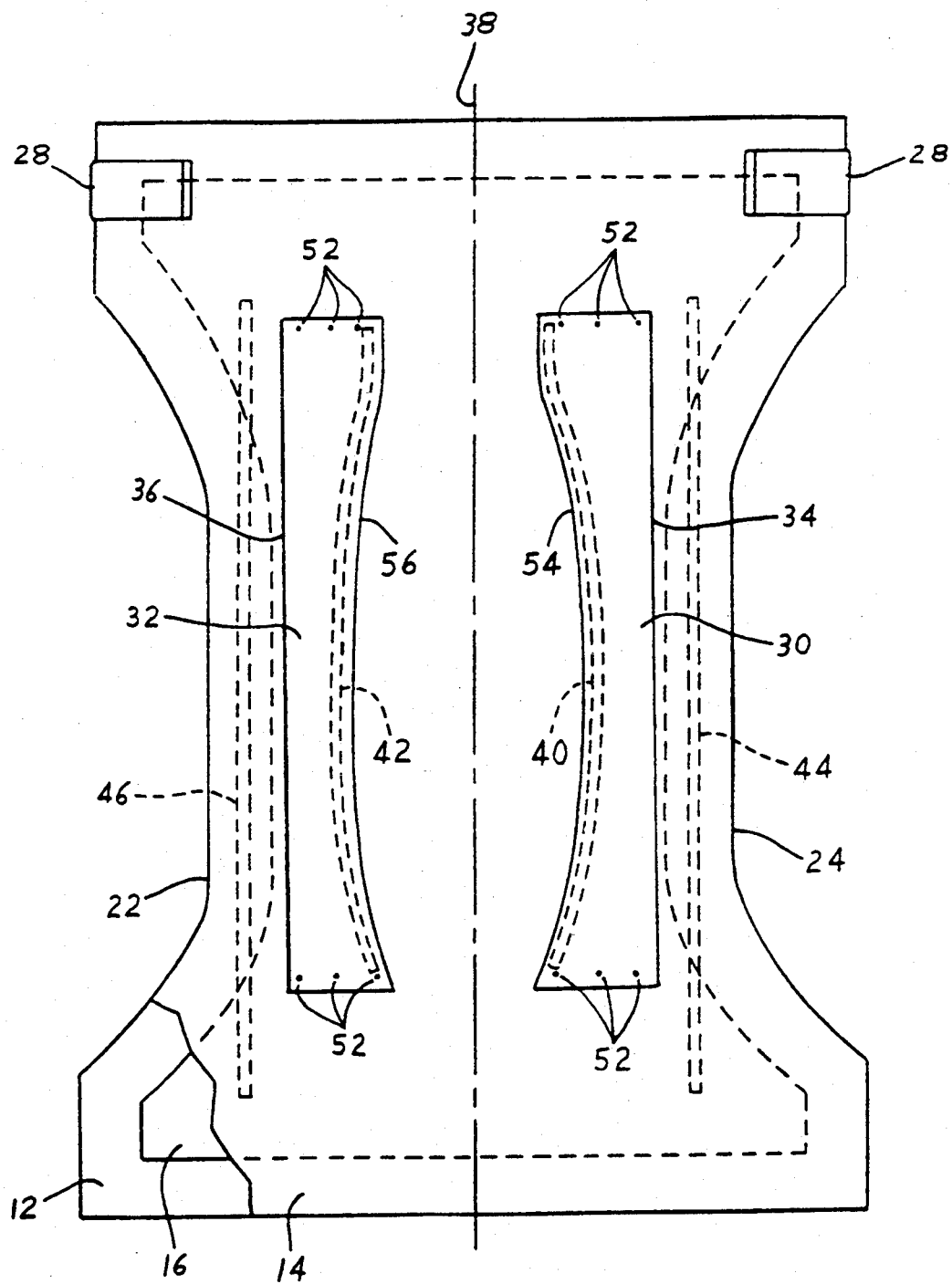
FIG. 8 is a plan view of a garment of the present invention showing partial flaps of varying width.

FIG. 8 is a plan view of still another alternative embodiment of the disposable garment of the present invention. This embodiment has flaps 30, 32 with varying width and with a length that extends from a first portion of the garment to a second portion of the garment where the total extent of the flaps is less than the full length of the garment. Typically, the flaps extend at least through the crotch section of the garment. Illustrated in FIG. 8 are flaps 30, 32, which have a width wider at respective ends of the flaps 30, 32 than at an intermediate portion of the flaps; however, it is comprehended within the scope of this invention that flaps 30, 32 may have a width wider at an intermediate portion of flaps than at respective ends. Also comprehended are combinations of the concepts described above wherein varying width flaps are attached to or formed from inner liner 14 along curved lines which converge to or diverge from centerline 38.

Thus, while the invention has now been described with reference to several preferred embodiments and illustrated with regard to a range of optional features, those skilled in the art will appreciate that various substitutions, omissions, modifications and changes may be made without departing from the spirit hereof. Accordingly, it is intended that the foregoing description be deemed merely exemplary of the preferred scope of the present invention and not to be deemed a limitation thereof.

I claim:

1. An integral disposable absorbent article comprising:
   a liquid pervious topsheet having a top surface;
   a backsheet connected to the topsheet;
   an absorbent core disposed between the topsheet and the backsheet;
   a pair of electrically contractible gasketing cuffs, each disposed adjacent to a longitudinal edge of the absorbent article, and having between them a longitudinal centerline;
   a pair of barrier cuffs,
   (a) each barrier cuff having a proximal edge and a distal edge,
   (b) each barrier cuff being disposed inboard of one of the gasketing cuffs,
   (c) at least a portion of each barrier cuff being attached to the top surface, and
   (d) a central portion of the distal edge of each barrier cuff being directed, by means of said portions being attached to the top surface, toward the longitudinal centerline of the integral disposable absorbent article, between the gasketing cuffs of the integral disposable absorbent article; and
   means for tensioning the barrier cuffs, to space a portion of the distal edge of each barrier cuff away from the top surface of the topsheet, whereby a channel is formed by the two barrier cuffs and a portion of the topsheet between the barrier cuffs.

2. The integral disposable absorbent article of claim 1, wherein the tensioning means comprises an elastic member.

3. The integral disposable absorbent article of claim 1, wherein the distal edges of each barrier cuff have contractible lengths, and wherein the tensioning means comprises means for contracting the length of the distal edges of each barrier cuff.

4. The integral disposable absorbent article of claim 1, wherein the backsheet is connected directly to the topsheet.

5. The integral disposable absorbent article of claim 1, wherein the backsheet is connected indirectly to the topsheet.

6. An integral disposable absorbent article having a front waist region, a back waist region, a crotch region between the front and back waist regions and two longitudinal edges, the longitudinal edges of the absorbent article being the edges which extend from the front waist region along the crotch region tot he back waist region; the absorbent article comprising:
   a liquid pervious topsheet having a top surface;
   a backsheet connected tot he topsheet;
   an absorbent core disposed between the topsheet and the backsheet;
   an elastically contractible gasketing cuff disposed adjacent each longitudinal edge of the absorbent article in at least the crotch region, the gasketing cuffs having between them a longitudinal centerline;
   a barrier cuff disposed adjacent each of the gasketing cuffs, each of the barrier cuffs having a proximal edge and distal edge, the proximal edges being disposed laterally inboard of the gasketing cuffs, at least a portion of each barrier cuff being attached tot he top surface, and a central portion of the distal edge of each barrier cuff being directed, by means of said portions being attached to the top surface, toward the longitudinal centerline of the integral disposable absorbent article, between the gasketing cuffs of the integral disposable absorbent article; and
   means for tensioning the barrier cuffs, to space a portion of the distal edge of each barrier cuff away from the top surface of the topsheet, whereby a channel is formed by the two barrier cuffs and a portion of the topsheet between the barrier cuffs.

7. The integral disposable absorbent article of claim 6, wherein the tensioning means comprises an elastic member.

8. The integral disposable absorbent article of claim 7, wherein the tensioning elastic member is an elastic strand.

9. The integral disposable absorbent article of claim 6, wherein the distal edges of each barrier cuff have contractible lengths, and wherein the tensioning means comprises means for contracting the length of the distal edges of the barrier cuffs.

10. The integral disposable absorbent article of claim 6, wherein the barrier cuffs are integral with the topsheet.

11. The integral disposable absorbent article of claim 6, wherein the barrier cuffs are unitary with the topsheet.

12. The integral disposable absorbent article of claim 6, wherein the barrier cuffs each have two ends, and additionally comprising adhesive means disposed adjacent each of the ends of the barrier cuffs for securing a portion of each barrier cuff, a portion of the distal edge of each barrier cuff in at least the crotch region remaining free from attachment so as to be spaced away from the top surface of the topsheet.

13. The integral disposable absorbent article of claim 6, wherein the backsheet is connected directly to the topsheet.

14. The integral disposable absorbent article of claim 6, wherein the backsheet is connected indirectly to the topsheet.

15. An integral disposable absorbent article having a front waist region, a back waist region, a crotch region between the front and back waist regions and two longitudinal edges and a longitudinal centerline, the longitudinal edges and longitudinal centerline of the absorbent article being the edges and centerline which extend from the front waist region along the crotch region to the back waist region; the absorbent article comprising:
- a liquid pervious topsheet having a top surface;
- a backsheet connected tot he topsheet;
- an absorbent core having side edges, the absorbent core being disposed between the topsheet and the backsheet;
- an elastically contractible gasketing cuff disposed adjacent each longitudinal edge of the absorbent article, each gasketing cuff comprising a flexible side flap extending from and along the side edges of the absorbent core in at least the crotch region of the absorbent article, and a flap elastic member secured to the side flap in an elastically contractible condition, whereby the elastically contractible gasketing cuffs form effective barriers about a wearer's legs;
- a barrier cuff disposed adjacent each of the gasketing cuffs in at least the crotch region, each of the barrier cuffs having a proximal edge and a distal edge, the proximal edges disposed in the side flaps between the flap elastic member and the side edges of the absorbent core in at least the crotch region, the distal edges being free from attachment in at least the crotch region, at least a portion of each barrier cuff being attached to the tops surface, and a central portion of the distal edge of each barrier cuff being directed, by means of said portions being attached to the top surface, toward the longitudinal centerline of the integral disposable absorbent article, between the gasketing cuffs of the integral disposable absorbent article; and
- a spacing elastic member secured to each barrier cuff for elasticizing and tensioning the barrier cuffs so that the distal edges of the barrier cuffs are spaced away from the top surface of the topsheet, whereby a channel is formed by the two barrier cuffs and a portion of the topsheet between the barrier cuffs;
- the elastically contractible gasketing cuffs and the barrier cuffs presenting an effective means against soiling of a wearer's garments.

16. The integral disposable absorbent article of claim 15, wherein the barrier cuffs each have two ends, and additionally comprising adhesive means, disposed adjacent each end of each of the barrier cuffs in the front and back waist regions, for securing the end portions of the distal edges of the barrier cuffs, a portion of the distal edge of each barrier cuff remaining free to be spaced away from the top surface of the topsheet in at least the crotch region.

17. The integral disposable absorbent article of claim 15, wherein the flap elastic member is curvilinear.

18. The integral disposable absorbent article of claim 15, wherein the barrier cuffs are integral with the topsheet.

19. The integral disposable absorbent article of claim 15, wherein the barrier cuffs are integral with the side flaps.

20. The integral disposable absorbent article of claim 15, wherein the backsheet is connected directly to the topsheet.

21. The integral disposable absorbent article of claim 15, wherein the backsheet is connected indirectly to the topsheet.

22. An integral disposable absorbent article comprising:
- a liquid pervious topsheet having a top surface;
- a backsheet connected to the topsheet;
- an absorbent core disposed between the topsheet and the backsheet;
- a pair of elastically contractible gasketing cuffs disposed adjacent to longitudinal edges of the absorbent article and on opposite sides of a longitudinal centerline of the absorbent article;
- a pair of barrier cuffs connected to the liquid pervious topsheet, each barrier cuff having a proximal edge and a distal edge, the proximal edges being disposed adjacent the gasketing cuffs and the distal edges being disposed inboard of the proximal edges, at least a portion of each barrier cuff being attached to the top surface, and a central portion of the distal edge of each barrier cuff being directed, by means of said portions being attached tot he top surface, toward the longitudinal centerline of the integral disposable absorbent article, between the gasketing cuffs of the integral disposable absorbent article; and
- means for tensioning the barrier cuffs, to space a portion of the distal edge of each barrier cuff away from the top surface of the topsheet, whereby a channel is formed by the two barrier cuffs and a portion of the topsheet between the barrier cuffs.

23. The integral disposable absorbent article of claim 22, wherein the backsheet is connected directly to the topsheet.

24. The integral disposable absorbent article of claim 22, wherein the backsheet is connected indirectly to the topsheet.

25. An integral disposable absorbent article, comprising:
- a liquid pervious topsheet having a top surface;
- a backsheet connected to the topsheet;
- an absorbent core disposed between the topsheet and the backsheet;
- a pair of elastically contractible gasketing cuffs, each of the gasketing cuffs being disposed adjacent to a longitudinal edge of the absorbent article and on opposite sides of a longitudinal centerline of the absorbent article;
- a pair of barrier cuffs, each barrier cuff
  (a) having a proximal edge and a distal edge;
  (b) being disposed inboard of one of the gasketing cuffs;
  (c) at least a portion of each barrier cuff being attached to the tops surface; and
  (d) being pervious to water vapor;
- a central portion of the distal edge of each barrier cuff being directed, by means of said portions being attached to the top surface, toward the longitudinal centerline of the integral disposable absorbent article, between the gasketing cuffs of the integral disposable absorbing article; and
- means for tensioning the barrier cuffs, to space a portion of the distal edge of each barrier cuff away from the top surface of the topsheet, whereby a channel is formed by the two barrier cuffs and a portion of the topsheet between the barrier cuffs.

26. An integral disposable absorbent article, comprising:
- a liquid pervious topsheet having a top surface;
- a backsheet connected tot he topsheet;
- an absorbent core disposed between the topsheet and the backsheet;
- a pair of elastically contractible gasketing cuffs, each of the gasketing cuffs being disposed adjacent to a longitudinal edge of the absorbent article and on opposite sides of a longitudinal centerline of the absorbent article;
- a pair of barrier cuffs, each barrier cuff
  - (a) having a proximal edge and a distal edge;
  - (b) being disposed inboard of one of the gasketing cuffs;
  - (c) at least a portion of each barrier cuff being attached to the top surface; and
  - (d) when placed in contact with wet skin of a wearer, permitting moisture to escape from the surface of the skin so contacted;
- a central portion of the distal edge of each barrier cuff being directed, by means of said portions being attached to the top surface, toward the longitudinal centerline of the integral disposable absorbent article, between the gasketing cuffs of the integral disposable absorbent article; and
- means for tensioning the barrier cuffs, to space a portion of the distal edge of each barrier cuff away from the top surface of the topsheet, whereby a channel is formed by the two barrier cuffs and a portion of the topsheet between the barrier cuffs.

* * * * *

UNITED STATES PATENT AND TRADEMARK OFFICE
CERTIFICATE OF CORRECTION

PATENT NO. : 5,415,644
DATED : May 16, 1995
INVENTOR(S) : Kenneth M. Enloe

Page 1 of 4

It is certified that error appears in the above-indentified patent and that said Letters Patent is hereby corrected as shown below:

On cover page, item [56], page 2, col. 1, line 12, delete "3,426,755" and substitute --3,426,756--.

On cover page, item [56] page 3, col. 2, line 23, delete "55-10169" and substitute --55-10,619--.

Please add the following patent documents:

| | | |
|---|---|---|
| -- 88/05,269 | 07/1988 | WO (PCT Patent Application) |
| 358,765 | 11/1931 | Great Britain |
| 476,600 | 1937 or 1938 | Great Britain |
| 616,419 | 1949 | Great Britain |
| 667,483 | 03/1952 | Great Britain |
| 790,062 | 02/1958 | Great Britain |
| 833,254 | 04/1960 | Great Britain |
| 849,573 | 09/1960 | Great Britain |
| 1,428,572 | 03/1976 | Great Britain |
| 1,453,870 | 10/1976 | Great Britain |
| 1,482,677 | 08/1977 | Great Britain |
| 1,520,017 | 08/1978 | Great Britain |
| 1,520,018 | 08/1978 | Great Britain |
| 1,543,915 | 04/1979 | Great Britain |
| 2,023,431 | 01/1980 | Great Britain |

UNITED STATES PATENT AND TRADEMARK OFFICE
CERTIFICATE OF CORRECTION

PATENT NO. : 5,415,644
DATED : May 16, 1995
INVENTOR(S) : Kenneth M. Enloe

It is certified that error appears in the above-indentified patent and that said Letters Patent is hereby corrected as shown below:

| | | |
|---|---|---|
| 2,051,557 | 01/1981 | Great Britain |
| 2,063,677 | 06/1981 | Great Britain |
| 2,080,093 | 02/1982 | Great Britain |
| 2,101,468 | 01/1983 | Great Britain |
| 2,103,093A | 08/1983 | Great Britain |
| 2,143,115 | 02/1985 | Great Britain |
| 2,149,289 | 06/1985 | Great Britain |
| 2,159,693 | 12/1985 | Great Britain |
| 2,161,059 | 01/1986 | Great Britain |
| 2,188,532 | 10/1987 | Great Britain |
| 2,193,625 | 02/1988 | Great Britain |
| 56-40,803 U | 09/1981 | Japan--. |

Column 4, line 36, after "article" insert --,--.

Column 4, line 42, delete "cone" and substitute --core--.

Column 4, line 58, after "section" delete "," and after "region" insert --,--.

Column 5, line 3, after "32" insert --, each barrier cuff or flap having a proximal edge and a distal edge,--.

UNITED STATES PATENT AND TRADEMARK OFFICE
CERTIFICATE OF CORRECTION

PATENT NO. : 5,415,644
DATED : May 16, 1995
INVENTOR(S) : Kenneth M. Enloe

It is certified that error appears in the above-indentified patent and that said Letters Patent is hereby corrected as shown below:

Column 5, line 13, delete "within" and substitute --without--.

Column 5, lines 25-26, delete "stability" and insert --ability--.

Column 6, line 34, after "4." insert --As shown in the drawings, and shown best in Figures 2 and 4, it is preferred that a central portion of the distal edge of each barrier cuff be directed, after manufacture of the absorbent article, toward the longitudinal centerline of the integral disposable absorbent article, between the gasketing cuffs of the integral disposable absorbent article.--.

IN THE CLAIMS

Col. 7, claim 1, line 38, delete "electrically" and substitute --elastically--.

Col. 8, claim 6, line 12, delete "tot he" and substitute --to the--.

Col. 8, claim 6, line 15, delete "tot he" and substitute --to the--.

Col. 8, claim 6, line 29, delete "tot he" and substitute --to the--.

UNITED STATES PATENT AND TRADEMARK OFFICE
CERTIFICATE OF CORRECTION

PATENT NO. : 5,415,644
DATED : May 16, 1995
INVENTOR(S) : Kenneth M. Enloe

It is certified that error appears in the above-indentified patent and that said Letters Patent is hereby corrected as shown below:

Col. 9, claim 15, line 13, delete "tot he" and substitute --to the--.

Col. 9, claim 15, line 35, delete "tops" and substitute --top--.

Col. 10, claim 22, line 26, delete "tot he" and substitute --to the--.

Col. 10, claim 25, line 58, delete "tops" and substitute --top--.

Col. 11, claim 26, line 6, delete "tot he" and substitute --to the--.

Signed and Sealed this

Twenty-sixth Day of March, 1996

Attest:

BRUCE LEHMAN

Attesting Officer

Commissioner of Patents and Trademarks